United States Patent [19]
Levis et al.

[11] Patent Number: 5,580,733
[45] Date of Patent: Dec. 3, 1996

[54] VAPORIZATION AND SEQUENCING OF NUCLEIC ACIDS

[75] Inventors: Robert J. Levis, Grosse Pointe Park; Louis J. Romano, Detroit, both of Mich.

[73] Assignee: Wayne State University, Detroit, Mich.

[21] Appl. No.: 301,732

[22] Filed: Sep. 6, 1994

Related U.S. Application Data

[63] Continuation of Ser. No. 748,851, Aug. 23, 1991, abandoned, which is a continuation-in-part of Ser. No. 648,282, Jan. 31, 1991, Pat. No. 5,210,412.

[51] Int. Cl.$^6$ .............. C12Q 1/68; C12P 19/34; G01N 33/48; B01D 59/44
[52] U.S. Cl. .............. 435/6; 435/91.1; 436/94; 436/173; 250/282; 250/423 P; 935/77; 935/78
[58] Field of Search .............. 435/6, 91.1; 436/94, 436/173; 250/282, 423 P

[56] References Cited

U.S. PATENT DOCUMENTS

| | | | |
|---|---|---|---|
| 4,716,105 | 12/1987 | Muzuuchi et al. | 435/5 |
| 4,729,947 | 3/1988 | Middendorf et al. | 435/6 |
| 4,782,296 | 11/1988 | Schmalbein et al. | 324/316 |
| 4,782,297 | 11/1988 | Schmalbein et al. | 324/316 |
| 4,812,763 | 3/1989 | Schmalbein | 324/316 |
| 4,816,571 | 3/1989 | Andrus et al. | 536/27 |
| 4,823,007 | 4/1989 | Hanson | 250/327.2 |
| 4,843,003 | 6/1989 | Henikoff et al. | 435/91 |
| 4,855,225 | 8/1989 | Fung et al. | 435/6 |
| 4,863,848 | 9/1989 | Blocker et al. | 435/6 |
| 4,863,849 | 9/1989 | Melamede | 435/6 |
| 4,865,968 | 9/1989 | Orgel et al. | 435/6 |
| 4,870,004 | 9/1989 | Conroy et al. | 435/6 |
| 4,889,799 | 12/1989 | Henikoff et al. | 435/6 |
| 4,988,879 | 1/1991 | Zare et al. | 250/423 P |
| 5,002,868 | 3/1991 | Jacobson et al. | 435/6 |
| 5,003,059 | 3/1991 | Brennan | 536/27 |
| 5,210,412 | 5/1993 | Levis et al. | 250/288 |
| 5,288,644 | 2/1994 | Beavis et al. | 436/94 |

FOREIGN PATENT DOCUMENTS 0360676  3/1990  France.

OTHER PUBLICATIONS

Spengler et al., Rapid Communications in Mass Spectrometry, 4,4 1990. pp. 99–102.
Worthy, C. and EN News, Sep. 17, 1990, pp. 21–23.
Prober et al., *Research Articles*, 238, (1987) pp. 336–341.
Nelson et al., Science, vol. 246, 22 Dec. 1989, pp. 1585–1587.
"Electrospray Ionization—Principles and Practice", Fenn, et al, *Mass Spectrometry Reviews*, 1990, 9, 37–70.
"Pulsed High–Pressure Liquid Injection of Biological Molecules, etc.", Pang, et al, *Applied Spectroscopy*, vol.42, No. 7, 1988, pp. 1200–1206.
"Volatilizaton of High Molecular Weight DNA by Pulsed Laser Ablation of Frozen Aqueous Solutions", Nelson, et al, *Science*, vol. 246, pp. 1585–1587, Dec. 22, 1989.
"Time–of–flight Mass Spectrometry: An Increasing Role in the Life Sciences", Robert J. Cotter, Biomedical & Environmental Mass Spectrometry, vol. 18, pp. 513–532 (1989).

*Primary Examiner*—Stephanie W. Zitomer
*Attorney, Agent, or Firm*—Reising, Ethington, Barnard & Perry

[57] ABSTRACT

Method for analyzing a nucleic acid molecule, without fragmenting the molecule, by vaporizing a mixture of the molecule and a matrix by illuminating the mixture with visible laser light absorbed by the matrix and not by the nucleic acid molecule. The method is useful for determining the nucleotide sequence of a polynucleotide by using mass spectrometry to determine the molecular weights of individual single-stranded nucleic acid molecules in a population including a plurality of single-stranded nucleic acid molecules generated from the polynucleotide, each molecule having a different molecular weight, and one defined terminus and one variable terminus which terminates at a specific nucleotide.

46 Claims, 10 Drawing Sheets

VAPORIZATION AND SEQUENCING OF NUCLEIC ACIDS

This application is a continuation of U.S. Ser. No. 07/748,851 filed Aug. 23, 1991, now abandoned, which is a continuation-in-part of Romano and Levis, entitled "Method For Analyzing An Organic Sample" filed Jan. 31, 1991, U.S. Ser. No. 648,282, now U.S. Pat. No. 5,210,412 assigned to the same assignee as the present application, and hereby incorporated by reference herein.

FIELD OF THE INVENTION

The present invention relates to methods for vaporizing nucleic acids, and for determining the nucleotide base sequence of a nucleic acid, e.g., deoxyribonucleic acid (DNA) or ribonucleic acid (RNA).

BACKGROUND OF THE INVENTION

DNA and RNA are single-stranded or double-stranded molecules formed as linear chains of nucleotide bases. DNA includes the nucleotides thymine (T), cytosine (C), adenine (A) and guanine (G), and RNA is formed from T, C, G and uracil (U). In double-stranded molecules the two strands are held together by hydrogen bonding between pairs of nucleotides, with A pairing with T or U, and C pairing with G. The bases in these base pairs are called complementary bases, and the two strands are called complementary strands.

The sequence of nucleotides along a strand of RNA or DNA is relevant to many scientific studies. For example, the sequence of bases is important to analysis of genetic disease in humans and other animals, and in diagnosis of such diseases.

DNA sequencing is generally carried out by the method of Sanger et al. (74 *Proc. Nat. Acad. Sci. USA* 5463, 1977) and involves enzymatic synthesis of single complementary molecules of DNA from a single-stranded DNA template and a complementary primer. Briefly, referring to FIG. 1, four separate syntheses are carried out. A single-stranded template is provided along with a primer which hybridizes to the template. The primer is elongated using a DNA polymerase, and each reaction terminated at a specific nucleotide via the incorporation of an appropriate chain terminating agent, for example, a dideoxynucleotide.

The four DNA synthesis reactions result in formation of four series of DNA molecules, each molecule having one defined terminus and one variable terminus. The defined terminus starts with the primer molecule. The variable terminus ends with a chain terminating agent specific for the nucleotide (either G, A, T, or C) at which the synthesis reaction terminated. The four different series of molecules are each separated on the basis of their molecule weight, in four separate lanes in a high resolution polyacrylamide gel, to form four series of bands, with each band on the gel corresponding sequentially to a specific nucleotide in the nucleotide sequence. Thus, the relative positions of the bands identify the positions in the DNA sequence of each given nucleotide base. Generally, the DNA molecules are labelled so that the bands produced are readily detected. As shown in FIG. 1, the intensity of the bands is generally non-uniform, within a single lane, because band intensity is directly related to the total number or concentration of DNA molecules of the same molecular weight in a specific lane, and this number varies from one molecule to another even when they are of approximately the same molecular weight and even when they contain the same chain terminating agent. Tabor and Richardson, U.S. Pat. No. 4,962,020, have recently described a method for producing uniform banding, by use of a manganese buffer.

Maxam and Gilbert, 74 *Proc. Nat. Acad. Sci. USA* 569, 1977 describe another method for sequencing DNA where chemicals are used to specifically cleave a DNA molecule and these cleavage products analyzed by gel electrophoresis.

Fluorescent labels can be used in place of radioactive labels, as described in Fung et al., U.S. Pat. No. 4,855,225 and Hunkapiller et al. U.S. Pat. No. 4,811,218, and Prober, et al., 238 *Science* 336, 1987. In addition, the DNA molecules may be labeled with different isotopic variants of an atom, e.g., sulfur. The sulfur atom is used as a marker for the specific nucleotide at the end of each nucleic acid molecule, and later identified by combustion of the molecule to produce sulfur dioxide, which is then detected using mass spectrometry. Brennan, U.S. Pat. No. 5,003,059; Jacobson et al., U.S. Pat. No. 5,002,868; and Serge, EPA 0 360 676 A1.

SUMMARY OF THE INVENTION

Applicants have discovered that high molecular weight nucleic acid molecules can be vaporized without fragmentation. In general, this vaporization is performed by use of a high energy visible laser light in conjunction with a high concentration of a matrix which absorbs the laser light energy. The nucleic acid molecule to be analyzed is mixed with the matrix prior to vaporization. When the laser light illuminates the matrix, the matrix is vaporized and any nucleic acid molecule within the matrix is entrained, i.e., simultaneously vaporized, along with the matrix. By selection of a suitable matrix, wavelength of laser light, and laser energy level, it is possible to ensure that little or no fragmentation of the nucleic acid molecule occurs. The matrix and wavelength of laser light should be such that the laser light is absorbed by the matrix but not absorbed by the nucleic acid molecule, and chemical bonds within the nucleic acid molecule are not cleaved. Applicants have found that use of high laser levels (above 80 mJ/cm$^2$, or even 300 mJ/cm$^2$) for vaporization produces significantly improved results than use of a lower laser energy.

This discovery allows the determination of molecular weights of nucleic acid molecules in a solution or in a solid state, and for the determination of the molecular weights of several different nucleic acid molecules within a mixture of nucleic acid molecules. To this end, the invention is particularly useful for determination the nucleotide sequence of DNA or RNA, without the need for any separation of nucleic acid molecules generated in a sequencing reaction.

For example, a population (series) of nucleic acid molecules can be formed by use of standard techniques, such as those described above, and directly analyzed by causing vaporization of each of the molecules and determination of their molecular weights. If four such populations of molecules, ending in A, T, G, or C, respectively, are created, the nucleotide sequence can be determined by comparing the molecular weights of molecules within each of the four populations. Such comparisons can be performed by use of a computer, and allow analysis of a large number of sequencing mixtures within a very short time.

Because analysis by mass spectrometry does not require separation of nucleic acid molecules from one another to obtain molecular weight, the methods of this invention provide significant advantages over prior sequencing methods which rely, in general, on use of polyacrylamide gel electrophoresis to separate the molecules. Thus, the sequencing methods described herein eliminate the most labor-intensive and time-consuming steps of DNA sequencing methods.

It is also possible, because of the enhanced sensitivity of this method, to substantially reduce the amount of reagents needed for sequencing. For example, sequencing can be performed with a reduced amount of a polynucleotide template and enzyme used in a dideoxy sequencing reaction. Applicants' method also provides significant time savings because mass spectrometry determinations can be made quickly. In addition, the technology described here can be easily automated for repeated sample analysis. Thus, the sequencing methods described herein have many advantages over currently available methods.

In general, a method of this invention features vaporization of a standard DNA sequencing solution containing nucleic acid molecules of varying molecular weights, modification of the vaporized molecules so that they are susceptible to analysis by mass spectrometry, for example, by ionization, and performance of mass spectrometry on the vaporized and ionized molecules.

Thus, in a first aspect, the invention features a method for analyzing a nucleic acid molecule, without fragmenting the molecule, by vaporizing a mixture of the molecule and a matrix by illuminating the mixture with visible laser light absorbed by the matrix and not by the nucleic acid molecule.

By "vaporizing" is meant that the nucleic acid molecule is caused to enter the vapor phase such that it is available for analysis by a mass spectrometer, or available for ionization and subsequent analysis by a mass spectrometer.

By "matrix" is meant any component of a mixture with the nucleic acid molecule which is adapted to absorb visible laser light, and can be vaporized by that laser light, and is adapted to simultaneously cause vaporization of the adjacent nucleic acid molecule. That is, the vaporized matrix entrains the embedded nucleic acid molecule and carries it into the vapor phase. Generally, this matrix is vaporized by visible laser light having a wavelength between about 400 and 1100 nanometers, preferably between 500 and 550 nanometers, and most especially 532 nanometers, which is not absorbed by the nucleic acid molecule.

In a related aspect, the invention features a method for determining the nucleotide sequence of a polynucleotide by using mass spectrometry to determine the molecular weights of individual single-stranded nucleic acid molecules in a population. The population includes a plurality of single-stranded nucleic acid molecules generated from the polynucleotide (e.g., by a sequencing technique described above), each nucleic acid molecule having a different molecular weight and one defined terminus and one variable terminus which terminates at a specific nucleotide. Generally, this method is performed without prior separation of the nucleic acid molecules from each other.

By "mass spectrometry" is meant any technique which allows the molecular weight of a nucleic acid molecule in the vapor phase to be determined. Those of ordinary skill in the art will recognize that many specialized apparatus, generally termed mass spectrometers, are known which are specifically adapted to perform the technique of mass spectrometry, e.g., a time-of-flight mass spectrometer which is particularly suited to detection of molecular weight of large molecules.

As discussed above, methods for generating nucleic acid molecules from a polynucleotide to determine nucleotide sequences are well known in the art. For example, such techniques include the use of a chain termination agent in a technique generally called dideoxy chain termination sequencing (see, Sanger et al., supra, and Tabor and Richardson U.S. Pat. No. 4,795,699), or the technique generally described by Maxam and Gilbert, supra. It is particularly important in the sequencing method that molecules of one molecular weight be provided in approximately equal numbers to molecules of similar molecular weight as, for example, described by Tabor and Richardson, U.S. Pat. No. 4,962,020. Thus, the population includes several sets of nucleic acid molecules of identical molecular weights, each set having a different molecular weight from each other set.

Each of the nucleic acid molecules in the population has a defined terminus, that is, each molecule has an identical 3' terminus or 5' terminus containing a chain of identical nucleotides. Each molecule also has a variable terminus, that is, the other of the 3' or 5' terminus is different for each set of nucleic acid molecules within the population. As will be recognized by those of ordinary skill in the art, for each molecule in the population, the variable terminus generally ends in a specific identical nucleotide.

In preferred embodiments of the above aspects, the determining step includes vaporizing a mixture of matrix and the population of nucleic acid molecules derived from the polynucleotide to be analyzed. The mixture is vaporized by illuminating it with visible laser light absorbed by the matrix. As discussed above, the nucleic acid molecules are generated by chemical degradation of the polynucleotide, or by extension of a short polynucleotide, called a primer, complementary to a portion of the polynucleotide to be sequenced by a DNA polymerase (e.g., T7 DNA polymerase) in the presence of a chain terminating agent, e.g., a dideoxynucleoside triphosphate, preferably in the presence of manganese. The polynucleotide may be a DNA or RNA molecule.

In other preferred embodiments, the determining step includes comparing the molecular weight of the nucleic acid molecules, to provide a nucleotide sequence, e.g., by use of a computer; the vaporizing step is performed using a laser adapted to emit a pulse of light, e.g., with a power greater than about 80 mJ/cm$^2$, or preferably greater than about 120 mJ/cm$^2$, or most preferably greater than about 320 mJ/cm$^2$; the laser is a neodium yttrium aluminum garnet laser; and the pulse of light is less than 20 e.g. 10 nanoseconds, and preferably about 5 nanoseconds.

In yet other preferred embodiments, the matrix is an organic dye, e.g., rhodamine 6G, with a ratio of matrix weight to total nucleic acid molecule weight ranging from about 1:1 to 100,000:1, more preferably 1,000:1 to 25,000:1; the matrix may also be chosen from Rhodamine 6G, Rhomdamine 700 or 800, DTTCI, LC8800, DNTTCI, HDITCI, DDCI-4, and dibenzocyanane 45 or from any one of a number of chromophores which absorb light between 400–1100 nm; and each nucleic acid molecule is bonded to an ionizable chromophore which allows ionization of each molecule, e.g., a fluorescent dye, selected from the group including fluorescein, rhodamine, tetramethylrhodamine, sulforhodamine 101, nitrobenzo-2-oxa-1-diazaole, anthracene, pyrene, coumarin, acridone, N-5-dimethyl amino naphthene, and derivatives thereof (including iodoacetamide, maleimide, isothiocyanate and succinimidyl carboxylate) and the like. Most preferably, the chromophore absorbs light of a wavelength greater than 300 nanometers, and is connected to the molecules by covalent bonding or by a linker arm (see e.g., Hunkapiller et al., U.S. Pat. No. 4,811,218 and Fung et al., U.S. Pat. No. 4,855,225), and preferably positioned between 1 and 50 atoms from the molecule.

Rhodamine 700 has the chemical formula $C_{26}H_{26}N_2O_5ClF_3$. It has the following structure:

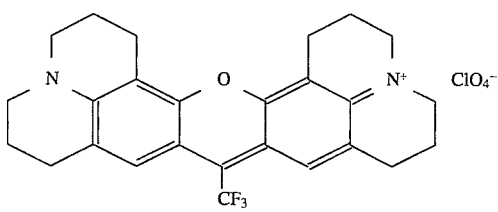

Rhodamine 800 has the chemical formula $C_{26}H_{26}N_3O_5Cl$. It has the following structure:

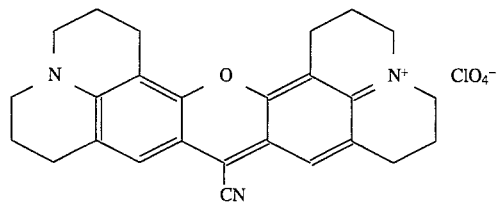

The compound DTTCI has the chemical formula $C_{25}H_{25}N_2S_2I$. It has the chemical structure:

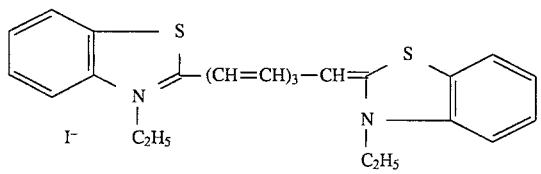

LC8800 is known as IR144 and has the chemical formula $C_{56}H_{73}N_5O_8S_2$. It has the chemical structure:

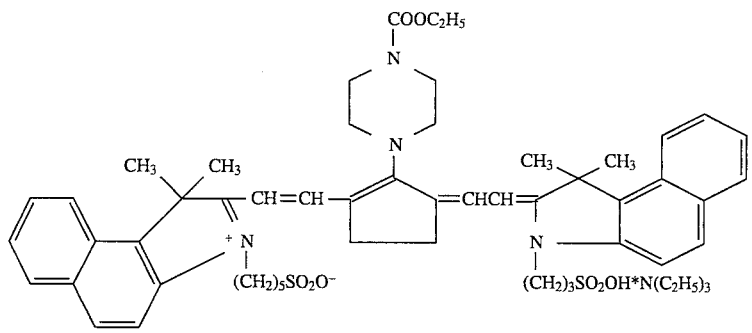

The material DNTTCI has the chemical formula $C_{30}H_{33}N_2S_2I$. It has the following chemical structure:

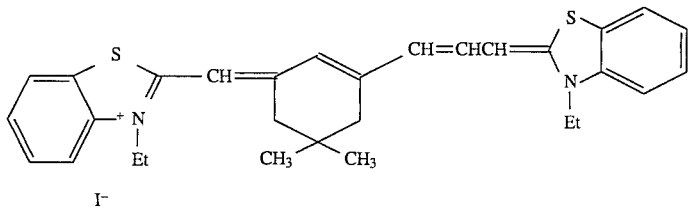

The material HDITCI has the chemical formula $C_{37}H_{37}N_2I$. The compound has the following structure:

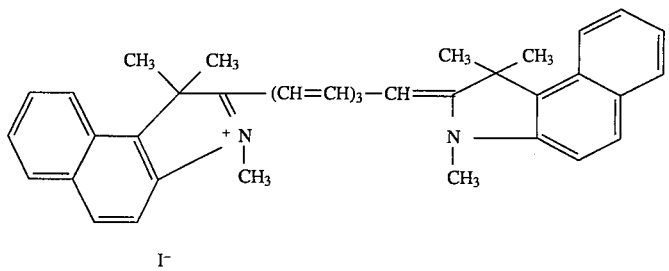

DDCI-4 has the chemical formula $C_{27}H_{27}N_2I$. It has the chemical structure:

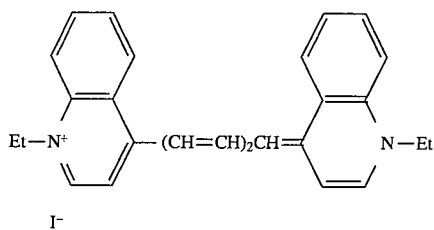

Dibenzocyanie 45 is also known as DDTTCI and has the chemical formula of $C_{33}H_{29}N_2S_2I$. It also has the following chemical structure:

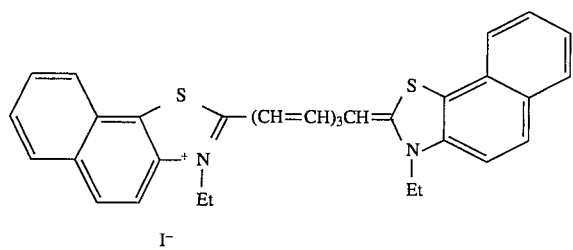

Rhodamine 6G has the chemical formula $C_{28}H_{31}N_2O_3Cl$. The structure is as follows:

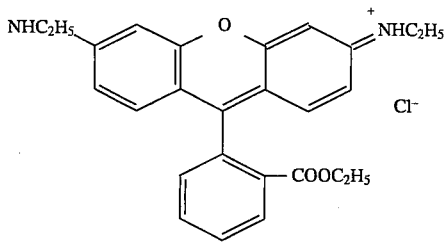

Other preferred embodiments, further include ionizing the nucleic acid molecules, after the vaporizing step, and determining the molecular weight of the vaporized ionized nucleic acid molecules using a mass spectrometer, e.g., a time-of-flight spectrometer. Preferably, a single positive charge is placed on each vaporized nucleic acid molecule prior to analysis by mass spectrometry. One technique for placing such a single positive charge is by resonance-enhanced multiphoton ionization (REMPI).

In another related aspect, the invention features an apparatus for determining the nucleotide sequence of a polynucleotide. The apparatus includes a mass spectrometer adapted to determine the molecular weight of individual single-stranded nucleic acid molecules (derived from the polynucleotide) in a first plurality of different populations (e.g., four separate A, T, C, and G populations), each population including a second plurality of different single-stranded molecules, each having a different molecular weight and one defined terminus and one variable terminus, the variable terminus terminating at a specific nucleotide, with the variable terminus of each first plurality of different populations terminating at a specific nucleotide. Also provided is a computer adapted to compare the molecular weights of each of the molecules in the populations to provide the nucleotide sequence of the polynucleotide.

In a further related aspect, the invention features one or more populations of vaporized and ionized nucleic acid molecules including a plurality of different single-stranded nucleic acid molecules each having a different molecular weight and one defined terminus and one variable terminus, the variable terminus terminating at a specific nucleotide.

Other features and advantages of the invention will be apparent from the following description of the preferred embodiments thereof, and from the claims.

DESCRIPTION OF THE PREFERRED EMBODIMENTS

The drawings will first briefly be described.
Drawings

Figure 13A:
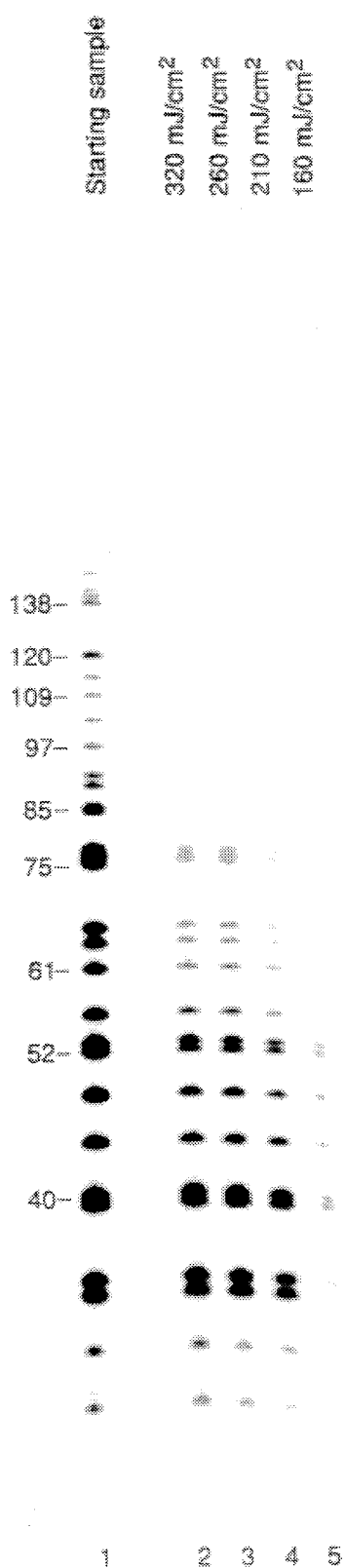
Figure 13B:
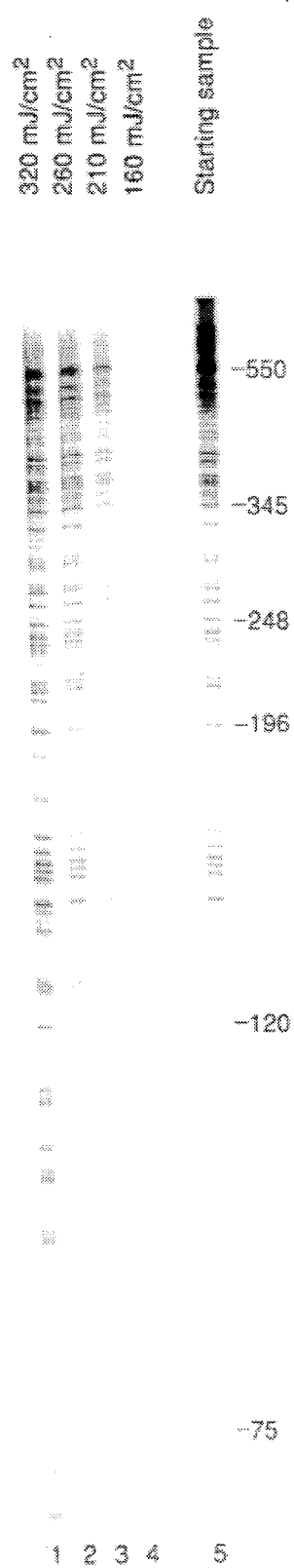
Figure 14:
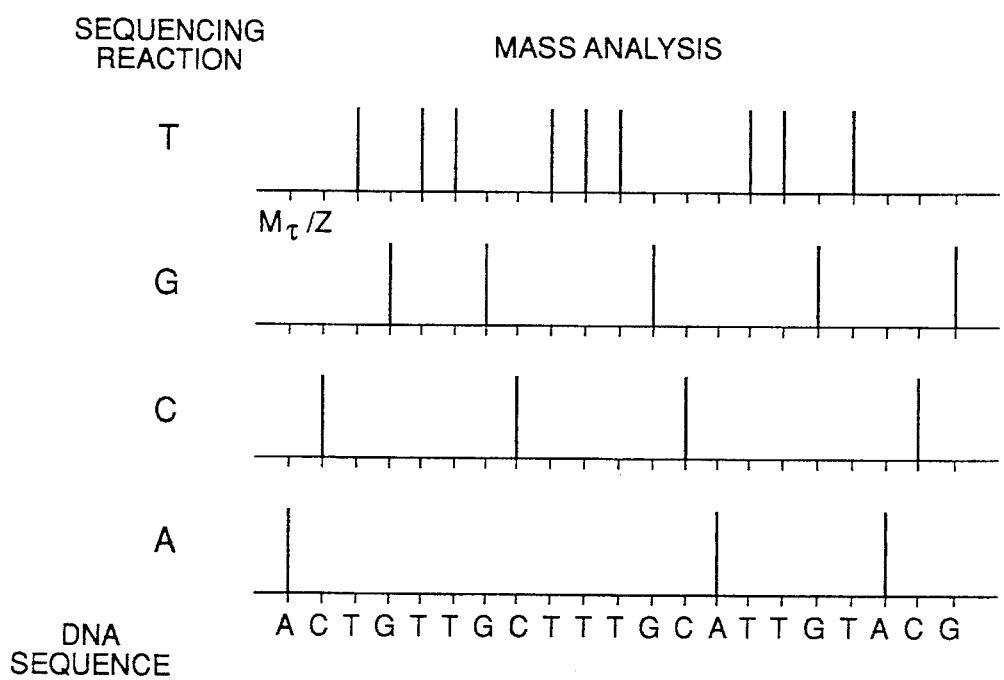

FIGS. 13A and 13B are copies of autoradiographs showing the effect of laser energy on populations of DNA molecules; and FIG. 14 is a diagrammatic representation of mock data from a mass spectrometer of the present invention, and its analysis to determine a nucleotide sequence. A, T, C and G represent the data obtained from populations of molecules having variable ends terminating in the corresponding nucleotide.

Vaporization Chromophore (Matrix)

It is important in the invention to mix the nucleic acid molecules to be analyzed with an excess of a matrix which is specifically chosen to absorb light energy at a wavelength not absorbed by the molecules. It is believed that the matrix absorbs the extremely high-powered light that is present in a short laser pulse (less than 10 nanoseconds (ns), most preferably less than 5 ns) and is thereby vaporized. Examples of such matrices include Rhodamine 6G, Rhomdamine 700 or 800, DTTCI, LC8800, DNTTCI, HDITCI, DDCI-4, and dibenzocyanine 45. Applicants believe that, because the laser energy is received by the sample over only a short time, all of the nucleic acid molecules within the matrix are caused to enter the vapor phase by entrainment before any fragmentation of the nucleic acid molecules can occur.

Ionization Chromophore

The present invention provides laser vaporization methods to desorb liquid phase nucleic acid molecules into the gas phase, and laser ionization methods to resonantly ionize each nucleic acid molecule. Unmodified nucleic acid molecules are not readily ionized at wavelengths above 300 nm. Thus, an ionizable group is introduced onto each molecule. For example, a single chromophore is introduced into each nucleic acid molecule so that a single positive charge can be introduced on each vaporized nucleic acid molecule by resonance-enhanced multiphoton ionization (REMPI). For example, referring to FIG. 2, an uncharged nucleic acid molecule (M) is raised to an excited electronic state (M*) by a first photon, and then to an ionized state ($M^+$) by a second photon. These ions ($M^+$) can then be detected using time-of-flight (TOF) mass spectrometry.

If the nucleic acid molecules do not contain a suitable chromophore for REMPI, then a light-absorbing chromophore may be bound to them. There are a large number of chromophores which are appropriate for this ionization process. Suitable chromophores include fluorescein, rhodamine, tetramethylrhodamine, sulforhodamine 101 (Texas red) nitrobenzo-2-oxa-1-diazole, anthracene, pyrene, coumarin, acridone, N-5-dimethyl amino naphthene, and their derivatives and the like. Derivatives of each of these chromophores are commercially available (from Molecular Probes, Inc., Eugene, Oreg.) in forms that can be linked to modified nucleic acid molecules (e.g., containing an available amine or thiol group). Examples of such derivatives are described in Hunkapiller et al., U.S. Pat. No. 4,811,218 and Fung et al., U.S. Pat. No. 4,855,225, and include iodoacetamide, maleimide, isothiocyanate, and succinimidylcarboxylate and the like. The appropriate functionality on the nucleic acid molecule to link to the first two in this series is SH, while the latter two require an $NH_2$ group to be present on the nucleic acid molecule.

Standard procedures for chemically binding these types of chromophores to organic molecules using linker arms (chemical structures which are adapted to covalently bond with a chromophore to hold that chromophore at a distance from the polynucleotide) are described in Hunkapiller et al., U.S. Pat. No. 4,811,218 and Fung et al., U.S. Pat. No. 4,855,225. Amine-and thiol-containing nucleic acids can also be prepared and used to link to the appropriate reactive group on the chromophore. Nucleic acid molecules that contain either a reactive amine or thiol group at the 5' end are commercially available from many sources (e.g., Clonetech, Palo Alto, Calif.). These are linked to the corresponding reactive groups on the chromophores using standard procedures. There are also a number of commercially available polynucleotides which are coupled to fluorescent chromophores. For example, ABI (Foster City, Calif.) sells four oligonucleotides that are covalently linked to two fluorescein (fluorescein and 2', 7'-dimethoxy-4,5-dichlorofluorescein) and two rhodamine (tetramethylrhodamine and rhodamine X) derivatives.

It is desirable that the chromophore is positioned at least 1 atom and possibly up to 50 atoms away from the nucleic acid molecules strands by use of a linker arm of appropriate lengths.

The chromophores can also be covalently linked to a nucleotide. For example, when used for DNA sequencing, these nucleotides can be used as the four dideoxyribonucleotides containing the four bases A, C, G, and T. E. I. DuPont (Wilmington, Del.) sells the four dideoxynucleotides covalently attached to four different fluorescein dyes. ABI sells four dideoxynucleotides covalently attached to four rhodamine chromophores. Also, there are several standard procedures by which a dideoxynucleotide can be coupled to a chromophore. For example, synthesis of the dideoxy-TTP derivative can be accomplished by converting dideoxy-UTP (ddUTP) to 5-(3-amino)allyl ddUTP by the method described by Langer et al. 78 *Proc. Natl. Acad. Sci. U.S.A.*, 6633, 1981. The cytidine analog can be formed by converting dideoxyuridine to the 4-hexylamine derivative using a procedure similar to that described by Horn et al., 17 *Nucleic Acids Res.*, 6959, 1989, coupling to the NHS ester of a selected chromophore, followed by conversion to the triphosphate by one of several methods, e.g., as described by Kozarich et al., 12 *Biochemistry*, 4458, and Ruth et al., 20 *Mol. Pharmocol.*, 415, 1981. The dideoxyadenosine or guanosine derivatives can be similarly prepared by lithiation of the purine ring at C8 followed by alkylation with a suitably protected amine-containing alkylhalide Barton et al., *Tetrahedron Lett.*, 279, 1979. Alternatively, the adenosine derivative can be prepared by iodination at C7 of the adenosine derivative, dideoxytubercidin, followed by coupling to N-trifluoroacetylpropargylamine under Pd (O) catalysis. Robins et al., 48 *J. Org. Chem.*, 1854, 1983.

It is important that only one chromophore be attached to each nucleic acid molecule to ensure a single positive charge on each molecule after ionization. The chromophore procedures discussed above enable detection of the molecules by allowing the placement of precisely one unit of positive charge per nucleic acid molecule, permitting an exact determination of molecular weight. Single ionization of each molecule greatly simplifies the appearance of a mass spectrum of mixtures of nucleic acid molecules.

Figure 1:
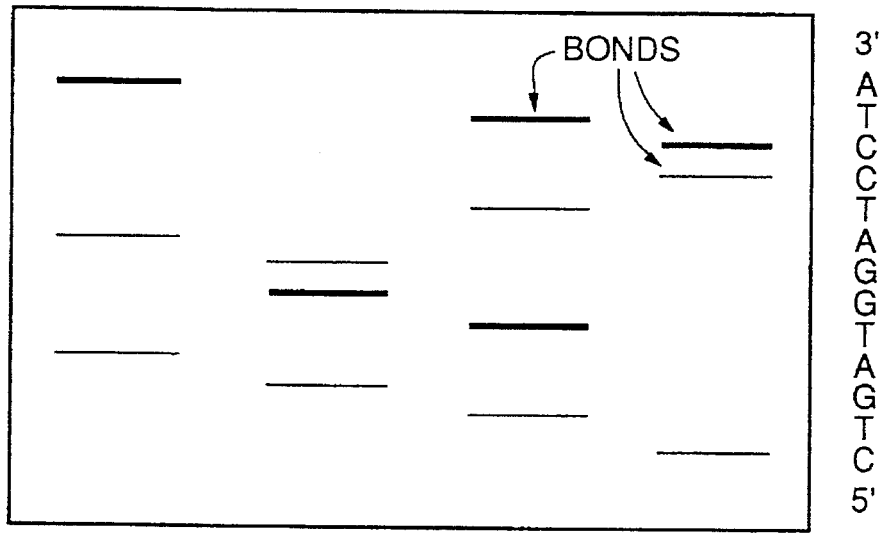
FIG. 1 is a diagrammatic representation of a dideoxy sequencing method.
Figure 2:
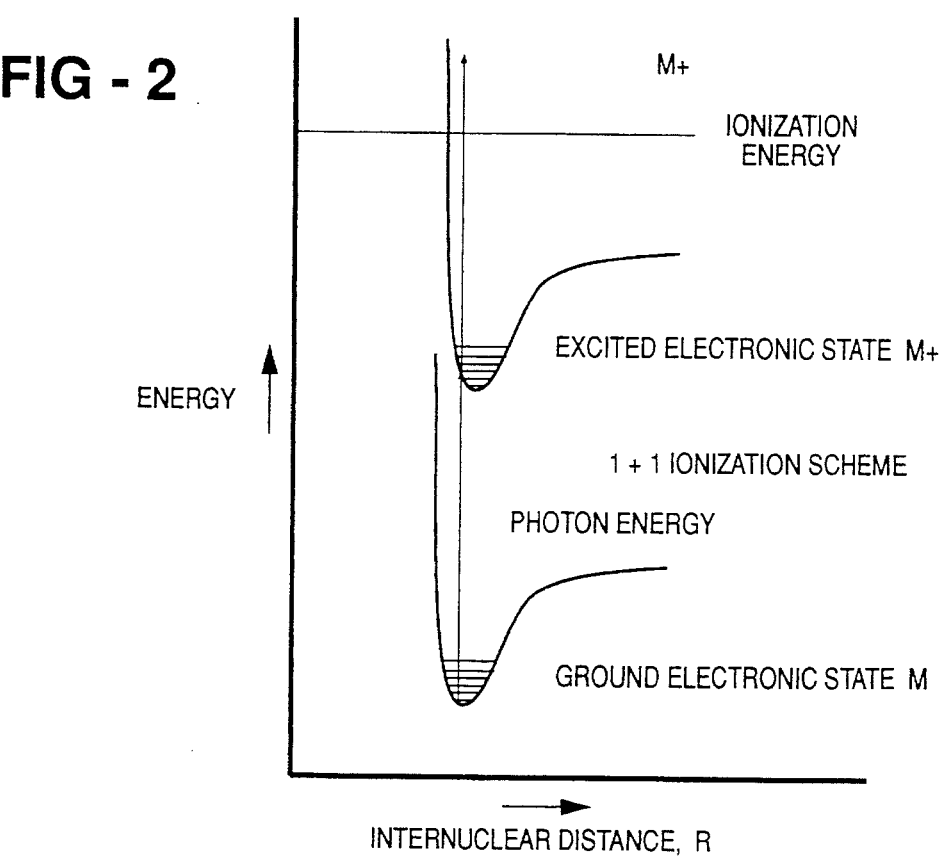
FIG. 2 shows a schematic view of 2-photon resonance enhanced ionization (REMPI) of a molecule M.

It is desirable that the chromophore absorb at a wavelength greater than 300 nm (where DNA weakly absorbs). In addition, the chromophore should have excited states which allow resonant ionization. In one example, when an anthracene chromophore is used, it is believed that the solution phase electron excitations may be centered around approximately 380 nm, 320 nm, and 280 nm. Thus, an ionization scheme as shown in FIG. 2 is possible.

Apparatus

Figure 3:
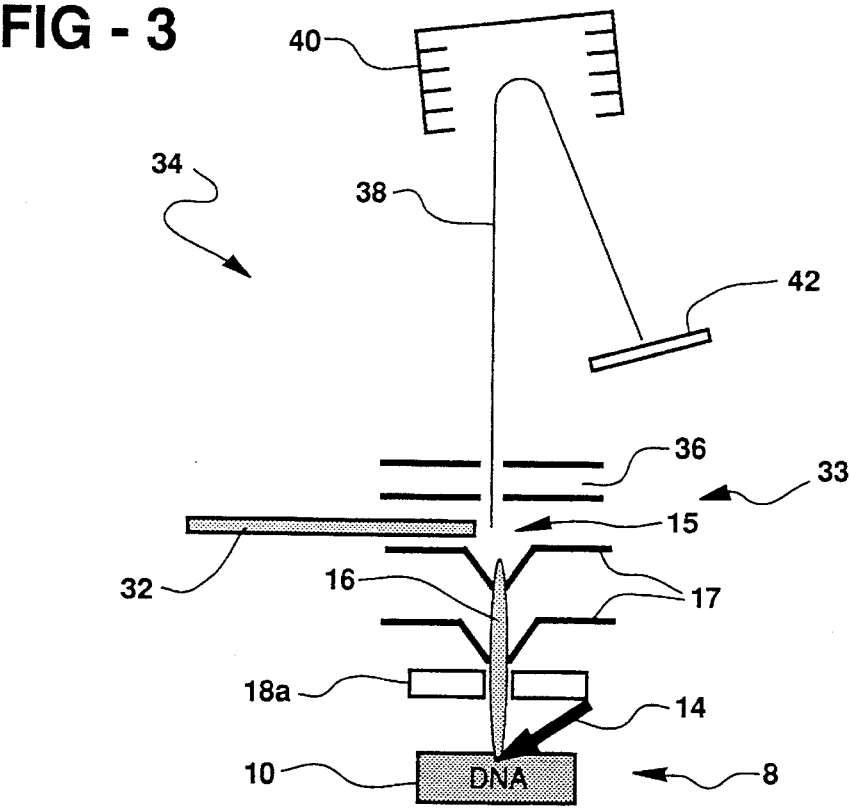
FIG. 3 is a schematic representation of an apparatus of the present invention.

Referring to FIG. 3, a schematic representation of an apparatus of the invention is provided. Specifically, apparatus 8 includes a sample holder 10 in which the nucleic acid molecule of interest is placed within a matrix. This sample holder is positioned to allow electromagnetic radiation, e.g. laser light, from a vaporization laser 14 to contact the nucleic acid molecule. Also provided is a pulsed nozzle 18A which is positioned relative to sample holder 10 to allow vaporized matrix and nucleic acid molecule to pass in a series of pulses as a desorbed sample (shown generally at 16) through a pair of beam skimmers 17 into a location 15 at which the volatilized nucleic acid molecules can be ionized by electromagnetic radiation from an ionization laser 32. Such ionized and vaporized nucleic acid molecules are then directed by use of a high voltage electric field 36 into a mass spectrometer (shown generally as 34) through an ion projectory 38 via an ion reflector 40 to a multi-channel detector 42.

Figure 4:
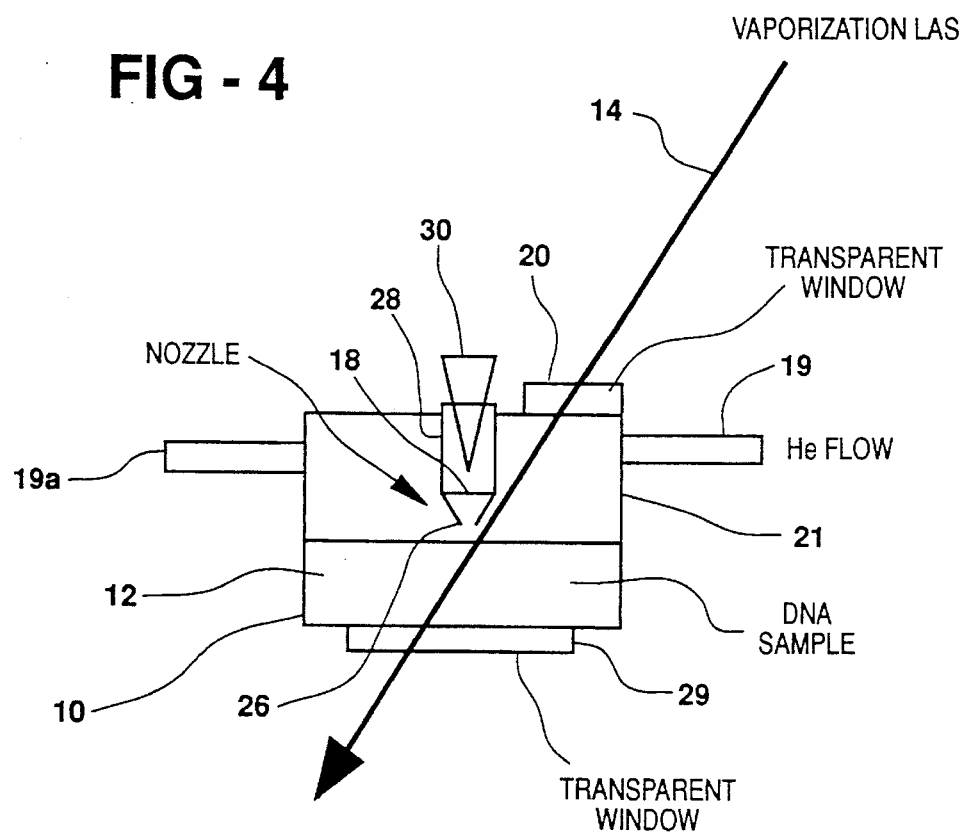
FIG. 4 is a schematic representation of a vaporization chamber of the apparatus in FIG. 3.

Referring to FIG. 4, a detail of a vaporization chamber used in apparatus 8 (shown in FIG. 3) is provided. This chamber includes the sample holder 10 on which aqueous sample 12 is deposited. Above this holder is a pulsed nozzle 18A which extracts gaseous sample resulting from vaporization of the sample by laser light from vaporization laser 14, together with the carrier gas, helium, which enters vaporization chamber 21 through inlets 19 and 19A. The carrier gas causes the vaporized sample to pass out of the vaporization chamber toward the laser beam of ionization laser 32 where the sample is ionized. A window 20 is provided in the upper portion of vaporization chamber 21, and a second transparent window 29 is provided in the lower portion of the chamber, to allow passage of laser light from vaporization laser light 14. The base of the pulse nozzle is shown generally by the numeral 26.

The vaporization chamber 21 shown in FIG. 4 can be maintained at either vacuum or ambient pressure. While not specifically shown, a high efficiency pumping system is provided to evacuate the low pressure chambers of this apparatus. Generally, the vaporization chamber is maintained at ambient pressure. When the sample is a liquid, the sample holder is oriented in a horizontal plane so that a liquid sample will not drip or run, and is situated so that it can be exposed to electromagnetic radiation. The sample holder is constructed from either polished 305 stainless steel or glass and is removable. It is affixed so that the sample can be reproducibly positioned in precisely the same location with respect to the pulsed nozzle. Alternatively, the sample can be dried to a solid by evacuation.

Figure 5:
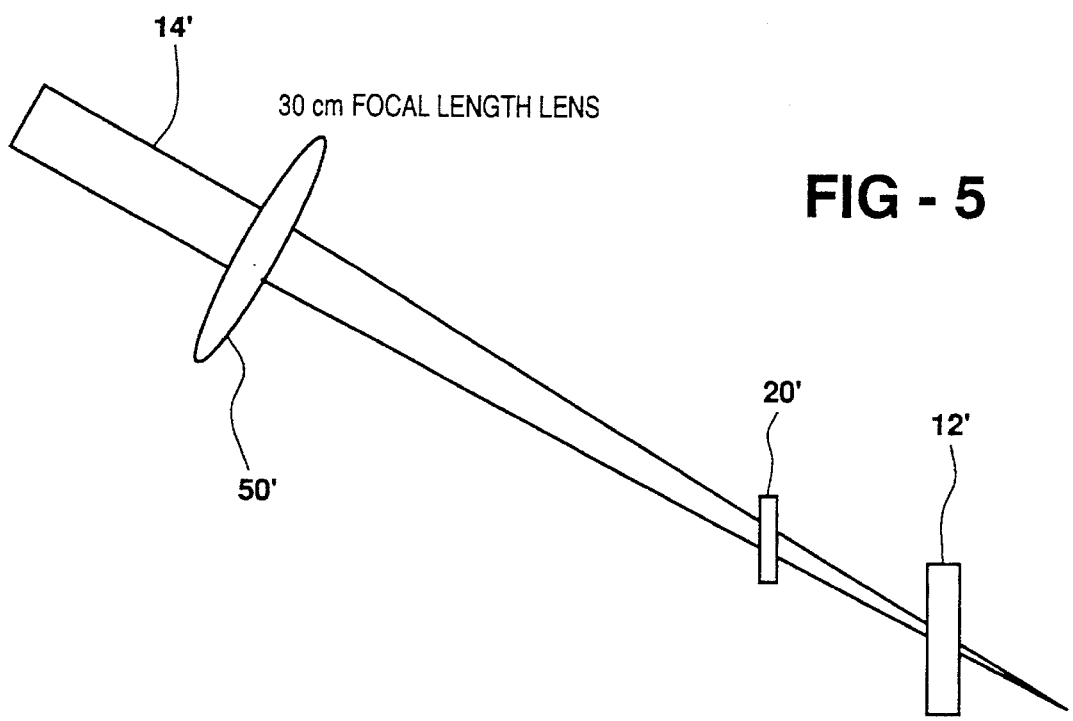
FIG. 5 is a schematic representation of an optical system for vaporization.

The source of the electromagnetic radiation to cause vaporization is generally a laser, e.g., a neodinium yttrium aluminum garnet (Nd YAG) laser. This laser is operated in a mode which provides radiation at 532 nm up to 500 mJ/cm$^2$. The light is columinated to provide high enough power to effect vaporization of at least a portion of the sample. FIG. 5 shows that the columinated light 14' from a laser is directed through an optical system. This systems includes two pellin broca prisms (not shown) which remove unwanted frequencies of light to a beam dump for removal. The remaining light is then directed, first through an iris to restrict beam size, and then through focusing optics 50 constructed from a nonabsorbing quartz S1 UV optical flat (1"×⅛") into the vaporization cell to impinge onto the sample from above. The laser is operated in such a manner so as to produce an intense flash of electromagnetic radiation which will be absorbed by the vaporization matrix and not the sample.

Once vaporized, as discussed briefly above, the sample is ejected into a helium atmosphere for subsequent processing. The helium injection and exhaust ports are positioned to maximize the flow of vaporized product toward the pulsed nozzle. The flow of helium is maintained using a He flow meter as supplied from Tylan Corporation. The output of the helium flow is connected to a pump via a metering valve. The pulsed valve is commercially available from Thermionics Laboratory, beam dynamics. The pulsed valve is positioned between 1 and 10 mm above the surface of the sample to be vaporized. The pulsed valve is timed to open 0.1 to 100 microseconds after the firing of the vaporization laser. The sample is extracted from the vaporization chamber into the ionization chamber, and a potential simultaneously applied to a 90% transmission grid to extract any ions which form during the vaporization process, and survive the transit through the pulsed nozzle.

Figure 6:
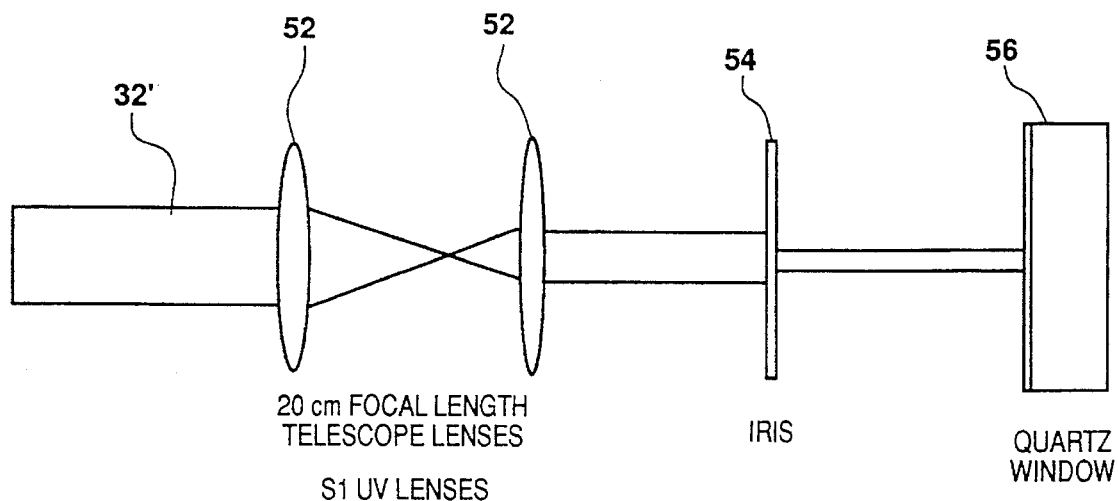
FIG. 6 is an optical system for REMPI.

Once the sample has entered the vacuum chamber, a second intense burst of electromagnetic radiation is delivered into the apparatus from an excimer or YAG laser source. In the preferred embodiment, the ionizing radiation is at 300–500 nm, most preferably 300–380, e.g., 345 nm. As shown in FIG. 6, this beam is developed using optical components. The beam 32' is directed through a telescoping cylindrical lens 52 to shape the beam into a compact pulse. The beam is then passed through slits 54 to define the final shape of a ribbon of about 1 mm×5 mm in size. The beam is then directed through a quartz window 56 into the vacuum chamber. In the vacuum chamber, the light intersects the beam of sample and matrix molecules at a 90-degree angle. The sample absorbs the radiation and the contained molecules ionized by resonant multiphoton processes.

The ionized sample is extracted by a three kilovolt potential applied to a 90% transmission grid (see FIG. 3, field 36) which is 10 cm from the plane of the ionizing radiation. The ions formed in the electromagnetic pulse are then extracted into a mass spectrometer 34 (FIG. 3), e.g., a time-of-flight mass spectrometer, such as a Bruker TOF 1 (Bruker Instruments, Inc. of Billerica, Mass.). This system operates at 30 Hz, with a very large sample depth (128K) and high resolution (16 bit). This system includes the required electronic controls and an ultra high vacuum pumping system that can be used for the ionization chamber.

Methods

The polynucleotide to be sequenced is processed according to the Sanger dideoxy sequencing reaction method described above, or any other sequencing method. These reactions are preferably run with a light absorbing chromophore linked to either the primer or the dideoxyribonucleotides. Each of the four enzymatic reactions containing the dideoxy-terminated molecule covalently linked to a light-absorbing chromophore is then mixed with an excess (e.g., 10–100,000 fold molar excess) of rhodamine 6G, and each of the four mixtures placed individually into the sample holder. When the sample is in the solid phase, the surrounding liquid medium, e.g., water, is removed by evaporation. When the sample is a liquid, the sample holder is placed directly into the vaporization chamber.

The sample is exposed to a 1–100 MW pulse from the laser at 532 nm which vaporizes the rhodamine 6G, and via entrainment, the nucleic acid molecule. This vaporized material is extracted through the pulsed nozzle by the helium stream, ionized by a 1 MW pulse from the excimer laser, and extracted by the three kilovolt potential applied to the 90% transmission grid into the time-of flight mass spectrometer. The molecular weights of the ions detected by the mass spectrometer are recorded. This process is then repeated in sequence for the remaining three dideoxy sequencing reactions, the results from the four samples are correlated, and the nucleotide sequence deduced. An example of such data is shown in FIG. 14. Correlation of these data can be performed manually or by computer using a program which determines the relative molecular weights of each molecule in each population of molecules. Such a program is readily formulated by those skilled in the art.

Those skilled in the art will understand that there are many variations of the above apparatus and method which fall within the purview of this invention. For example, different matrices can be used for the vaporization processes and different chromophores can be used for the ionization processes, as can different sources of electromagnetic radiation be used. The sample may require pre-treatment by various procedures to increase sensitivity levels, for example, removing the template polynucleotide, removing the substrate nucleotides, exchanging counterions, or removing any proteins prior to analysis. Furthermore, the sample holder and vaporization chamber can be modified so as to accept multiple samples by the addition of a movable stage that will bring each of the various samples into register for the vaporization step.

The following examples are illustrative of the invention. They were performed in the sequencing chamber shown in FIGS. 7 and 8. The chamber consists of a solid film vaporization system juxtaposed to a REMPI TOF chamber. With this vaporization system a 2 μl spot of a mixture of sample and rhodamine 6G is placed on a glass microscope slide, the sample allowed to dry and the glass slide fixed to a stainless steel rod sample holder. The spot is irradiated with a laser pulse and the vapor plume travels toward the electrostatic grid plates of the time-of-flight mass spectrometer.

Figure 7:
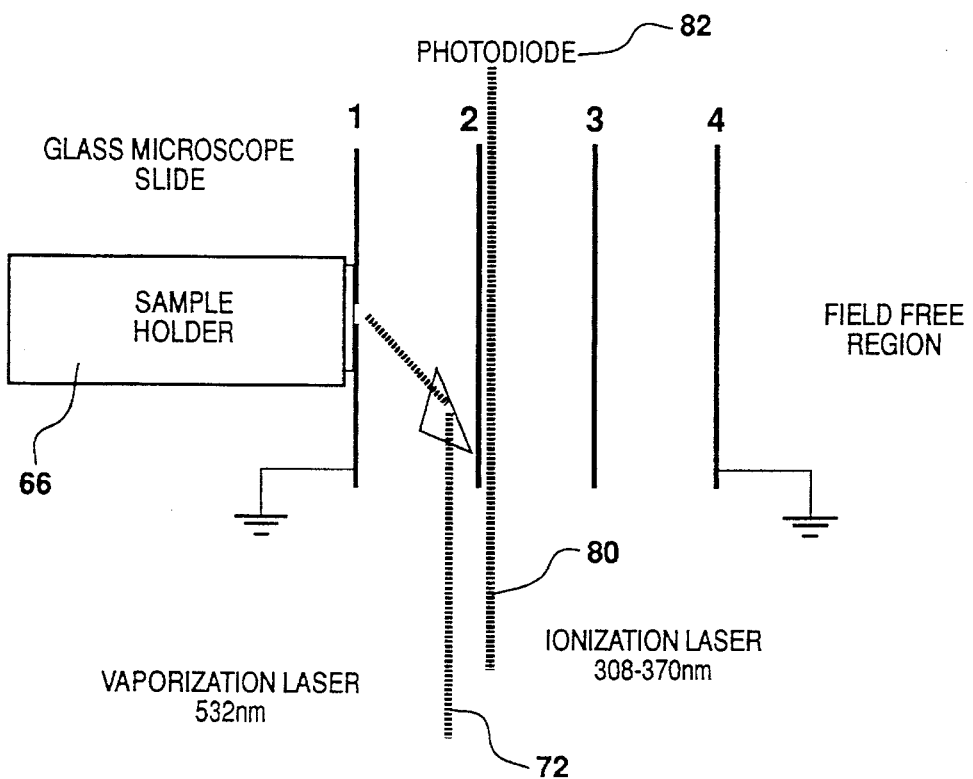
FIG. 7 is a side view of an apparatus of the present invention.

The lens system for the mass spectrometer is shown in FIG. 7. Four grid plates (1–4) form the acceleration optics. The following is a description of the ion optical system starting from the leftmost grid plate shown in FIG. 7. The first plate has a ⅛" aperture in its center. This plate is grounded for these examples. The next plate contains a 90% transmission grid which is typically biased positive 1000 volts with respect to ground. One function of this grid is to repel positively charged ions back to the ground plate so that only neutral molecules enter the ionization region of the mass spectrometer. The next plate is typically biased positively to 950 volts with respect to ground. The region between plates 2 and 3 is called the ionization region because the resonance-enhanced multiphoton ionization occurs here. This region also forms a low voltage extraction region for the dual slope acceleration scheme which serves to decrease the full-width-at-half-maximum of the signal peaks. The fourth plate contains a 82% transmission grid and is grounded. The region between plates 3 and 4 represents an acceleration of 950 eV per ion. The ions then enter a 63 cm field free drift region of the mass spectrometer.

At the end of the mass spectrometer is a high molecular weight ion detector 68. This consists of one stage from a CuBe electron multiplier detector. This "venetian" blind ion conversion stage is biased to 10 keV to convert high molecular weight ions to smaller ions and electrons. This type of ion conversion system has the added advantage of protecting the multichannel ion detector from carbonaceous contamination. The resulting particles are then directed to the microchannel plate detector for current amplification. The signal is amplified further in a fast amplifier/discriminator. The signal is then directed to a digital storage scope where current or signal is stored as a function of time. A plot of current vs. time forms the time-of-flight mass spectrum.

Figure 8:
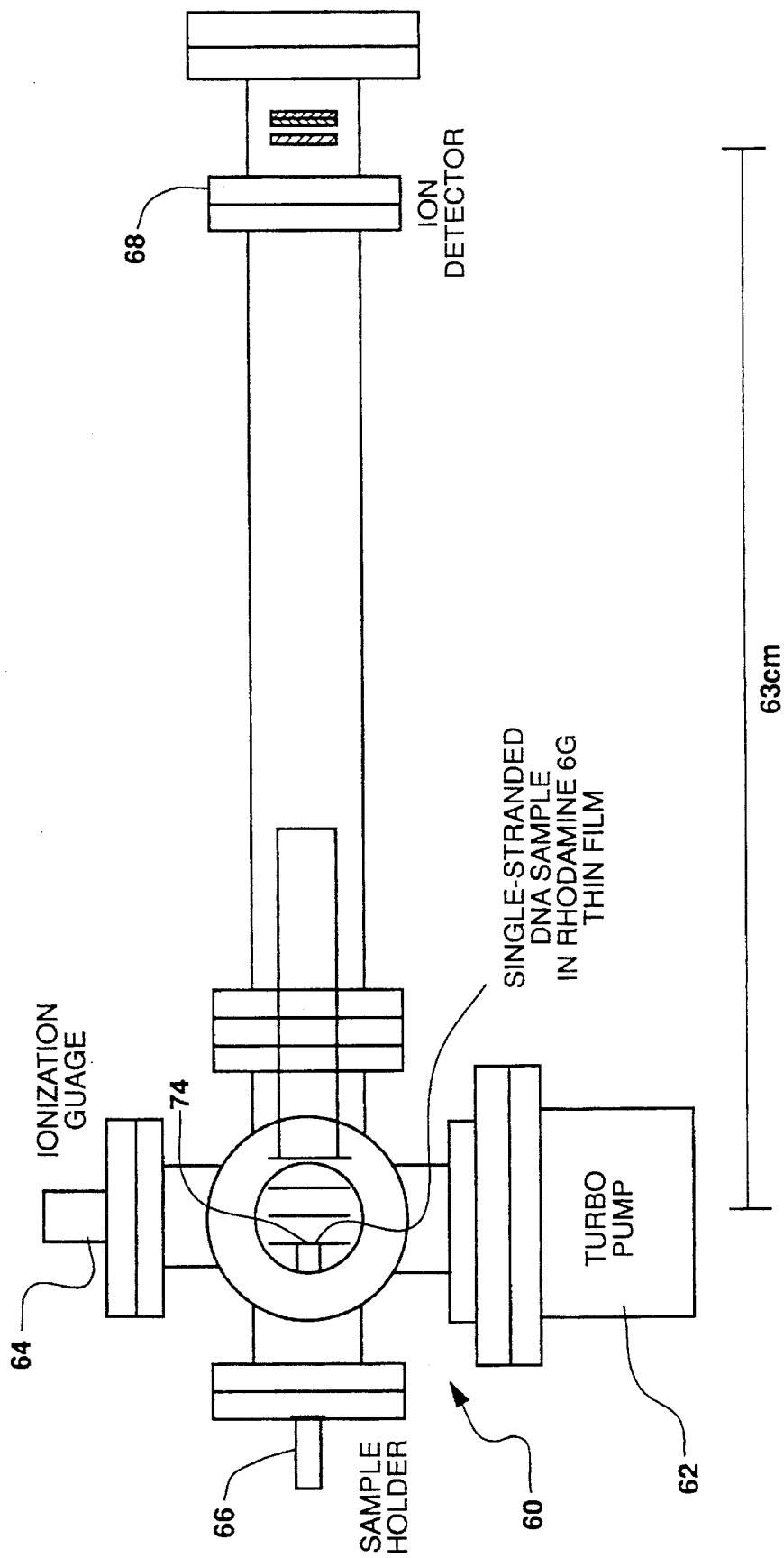
FIG. 8 is a top view of the apparatus of FIG. 7.

A schematic of the entire sequencing system is shown in FIG. 8. The vaporization chamber and TOF mass spectrometer are pumped by a turbo molecular vacuum pump. The laser beams necessary for ionization and vaporization enter through quartz windows. The optical setup allows the beams to enter the chamber through the same window. The vaporization laser is directed at the front of the thin film system by a turning prism, mounted as shown in FIG. 7. The ionization beam travels parallel to the plane of the extraction plates. The timing between the two laser pulses is maintained by precision delay circuits. The minimum vacuum for an experiment is approximately $1 \times 10^{-4}$ torr.

The DNA sample mixture 74 was spotted onto a glass coverslip attached to the end of the stainless steel sample positioner. The mixture of laser dye and tagged DNA sample was allowed to dry into a solid thin film on the coverslip. The sample was then loaded into the vacuum chamber and pumped to a pressure of approximately $5 \times 10^{-6}$ torr.

In both example 1 and example 2 described below, the vaporization laser struck the thin film at an angle of approximately 45 degrees from the surface normal. The vaporization laser used was the second harmonic of a Nd YAG III laser, (532 nm, 6 ns pulse length, variable power). The YAG laser was equipped with guassian optics so that the photon density within the beam was approximately constant across the diameter of the beam. The diameter of the vaporization laser beam was irised to 1 mm. The fluence of the beam ranged between 10 and 80 mJ/cm$^2$ as measured by a power meter (not shown). The sample positioning system was rotatable so that fresh sample could be continuously brought into the area of vaporization, if necessary.

A multiphoton ionization laser 80 was used to generate a 345–370 nm photon and 15 ns pulse length, which passed parallel to the plane of the thin film at a distance of 11 mm from the surface. The beam was irised and passed through 1 mm slits. The beam shape of this ionization laser was a ribbon having dimensions 1 mm×7 mm. For the experiments requiring ionization of the DNA sample, the excimer laser was triggered to fire at a time of 45 microseconds after the vaporization laser hit the target. The pulse of photons from the ionization laser was detected using a photodiode. The signal from the photodiode defined time=zero for the time-of-flight measurement.

EXAMPLE 1

Figure 9:
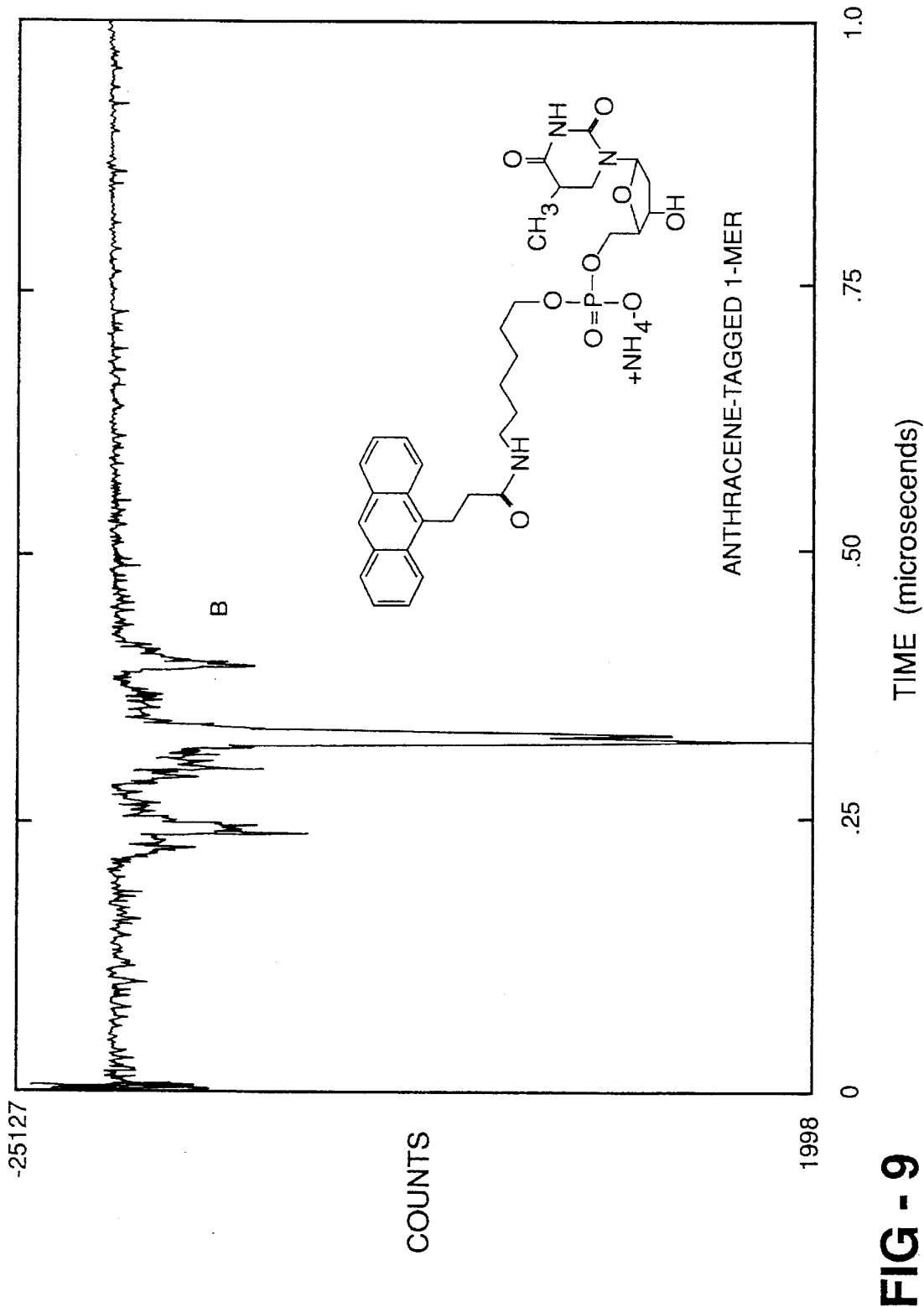
FIG. 9 is a spectrum of analyzed samples by use of the apparatus of FIGS. 7 and 8.

A sample of anthracene-labeled thymidine-5'-monotriphosphate was mixed at a 1 to 1 molar ratio with rhodamine 6G dye. The sample was then spotted onto the sample holder as described previously. The vaporization laser at 532 nm was directed onto the sample thin film with a fluence of 40 mJ/cm$^2$. The ionization laser at 345 nm was maintained at 30 mJ/cm$^2$. A representative time-of-flight spectrum prepared from the oscilloscope 86 connected to the multichannel detector inputs 68 and the photodiode 82 via lines 88 and 90, respectively, is shown in FIG. 9.

In this plot (FIG. 9), the current signal output from the multichannel detector was plotted as a function of time in microseconds. The peak appearing at 32.7 microseconds, labeled A, was identified as pure rhodamine 6G (MW=479 AMU) by control experiments where no labeled nucleotide was present.

When the anthracene-labeled nucleotide sample was added to the thin film, the peak at 41 microseconds, labeled B, appeared. This arrival time implied that a species of approximately 650 AMU was present in the vaporized sample. Therefore the mass calculated for the tagged nucleotide is 650 AMU.

EXAMPLE 2

In this example, the ion detection system of FIG. 7 was removed from the apparatus and a piece of filter paper installed to collect all of the laser vaporization materials. A 4 mm diameter hole was placed in the filter paper to allow passage of the vaporization laser. The paper was positioned at a distance of 10 mm from the vaporization spot on the thin film.

An oligonucleotide (50 pmol) having the sequence 5'-GTTTTCCCAGTCACGAC-3' was synthesized, purified by high pressure liquid chromatography (HPLC), and labeled at the 5' end with $^{32}$P using polynucleotide kinase. The labeled oligonucleotide was purified from unreacted ATP using a Waters Associates Sep-Pak C18 cartridge (Maniatis et al., Molecular Cloning, A Cloning Manual, Cold Spring Harbor Press, New York, 1982). The final specific activity of the oligonucleotide was 300 counts per minute per femtomole (cpm/fmol). Five picomoles (pmol) of the oligonucleotide was dissolved in 4 µl of water containing 10 mg/ml rhodamine 6G. This resulted in a final molar ratio of sample to matrix of 1:17,000. This mixture was then spotted in two 2 µl aliquots on a glass cover slip. The dried sample was placed in the sample chamber, the chamber evacuated to $5 \times 10^{-6}$ torr, and then the sample was exposed to the second harmonic of the Nd YAG III laser (532 nm, 8 ns pulse length) at a power equal to 130 mJ/cm$^2$. The filter containing the putative vaporized DNA was removed and the process twice repeated on fresh samples at power levels equal to 85 and 45 mJ/cm$^2$, respectively. Each filter was then exposed to Kodak XAR-5 X-ray film to obtain the distributions shown in FIG. 10: panel A, 130 mJ/cm$^2$; panel B, 85 mJ/cm$^2$; panel C, 45 mJ/cm$^2$.

Three features of the vaporization process are revealed by this analysis. First, as the laser power was increased, the amount of molecular vaporization product also increased. Second, the images of the vaporized material on the filter paper revealed a highly directional vaporization process. The distribution is peaked in the normal direction and was considerably tighter than a simple cosine distribution expected for a thermal desorption process. Third, the $^{32}$P present on the filter paper was evenly distributed, as is expected for molecular vaporization. Spallation, or the removal of macroscopic pieces of the mixture, has been shown in prior studies (Nelson et al., *Science* 1585, 1989) to lead to a spotted or speckled appearance. Spallation features, were observed in our experiment when vaporization was performed at atmospheric pressure on a liquid sample. Taken together, the images of the distribution obtained in these experiments strongly suggest that individual molecules were being vaporized.

EXAMPLE 3

To characterize the products obtained from the laser vaporization of the above 17-mer, the radioactive material on each filter (Example 2) was eluted by soaking in water, and each mixture then analyzed by polyacrylamide gel electrophoresis.

Figure 10A:
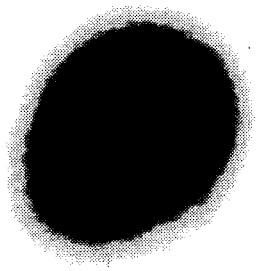
FIGS. 10A, 10B, 10C and 11 are copies of autoradiographs showing a vaporized oligonucleotide.
Figure 10B:
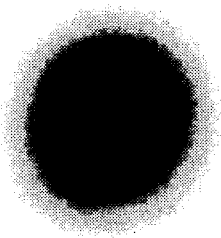
Figure 10C:
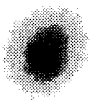

The autoradiographs of the filter papers shown in FIG. 10 were used to indicate where the vaporized radioactive oligonucleotide was deposited onto the filters. These portions were excised and then extracted with two 150 µl portions of water. The resulting solutions were concentrated, and loaded onto a 20% polyacrylamide gel: (FIG. 11) lane 1, 130 mJ/cm$^2$; lane 2, 85 mJ/cm$^2$; lane 3, 45 mJ/cm$^2$; lane 4 starting oligonucleotide. The gel was electrophoresed at 1000 V for 2 hr, and the positions of the bands determined by autoradiography. The positions of inorganic phosphate and nucleotide were determined by running authentic samples in adjacent lanes.

Figure 11:
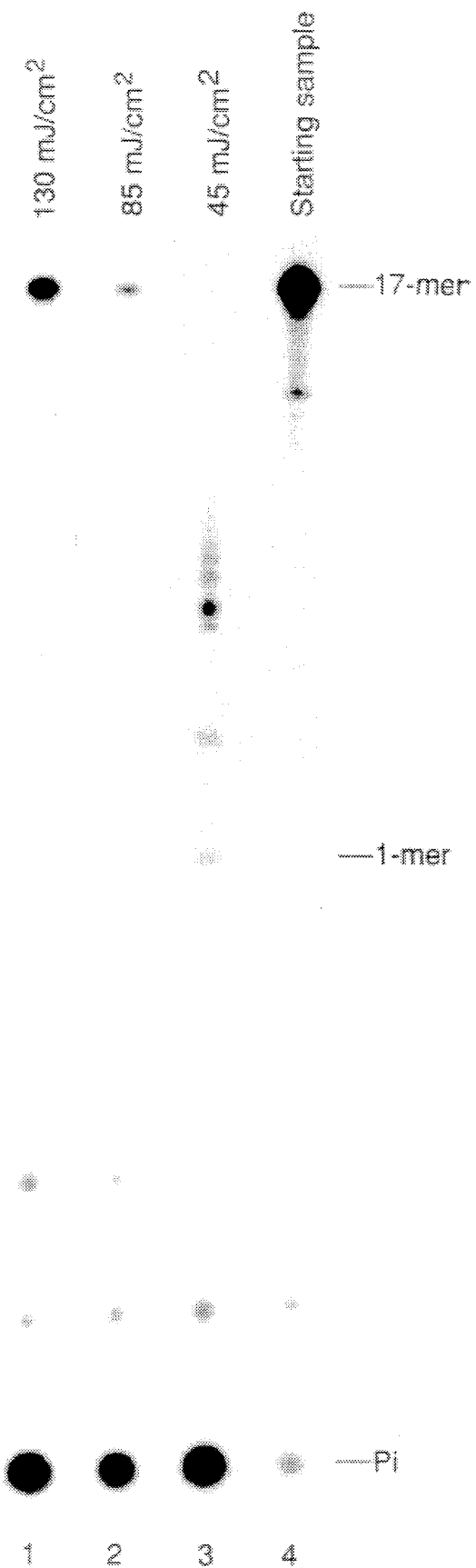

The sample vaporized using a laser power of 45 mJ/cm$^2$ showed extensive strand scission, giving rise to nucleic acid molecules having an average chain length of four nucleotides (FIG. 11, lane 3; cf. starting sample in lane 4). Applicants believe that strand breakage occurred through activation of the phospodiester bond. Also, a great deal of the label was observed as free inorganic phosphate ($P_i$). However, the samples vaporized at 130 and 80 mJ/cm$^2$ (FIG. 11, lanes 1 and 2) displayed no observable strand scission, although substantial amounts of phosphate were produced. There are several possible explanations for this observation. First, it is most likely that at lower laser powers the molecules remain in the thin film longer, causing the desorption process to mimic thermal decomposition, resulting in a much higher probability that bonds will be broken. Conversely, the vaporization process becomes a nonthermal, nonequilibrium photochemical process at high laser fluences. Second, the vaporized product should be less decomposed at high fluences because the density of desorbed material increases as the laser power increase. As the density increase, the number of cooling collisions increase an the vaporization process resembles a free jet expansion. A third possibility is that as the fluence of the vaporization beam increases, new electronic states in the desorbed rhodamine 6G are accessed via multiphoton absorption which serve to more efficiently transfer the nucleic acid molecules into the gas phase. This is supported by the fact that at the higher laser powers almost none of the laser dye travels to the filter paper without decomposition, whereas at lower incident fluxes much of the laser dye arrives intact.

EXAMPLE 4

To more fully characterize the bond-breaking process observed in the 17-mer experiment, the vaporization of [$\alpha$-$^{32}$P] dATP as a function of laser power was studied. [$\alpha$-$^{32}$-P] ATP (60 pmol, 3000 Ci/mmol) was dissolved in 20 µl of water containing 10% methanol and 10 mg/ml rhodamine 6G. Sample spots were prepared and vaporized as described above in Example 2 at powers equal to 320, 208, 180, 129, 85 and 45 mJ/cm$^2$ using a fresh spot for each power level. The resulting filters were processed as described above in Example 3, and the concentrated solutions adjusted so that each had 20,000 cpm/µl. Two microliters of each solution containing the materials which had been vaporized were then eluted from the filter papers, spotted onto a glass PEI-Cellulose F TLC plate (EM Science), and eluted with a solution of 0.6M LiCl in 1.0M formic acid. The plate was dried, and the amount of radioactivity present in each spot determined using an Ambis Radioactivity Image Scanner. The identity of the analyzed components was determined by cospotting with authentic samples.

Figure 12:
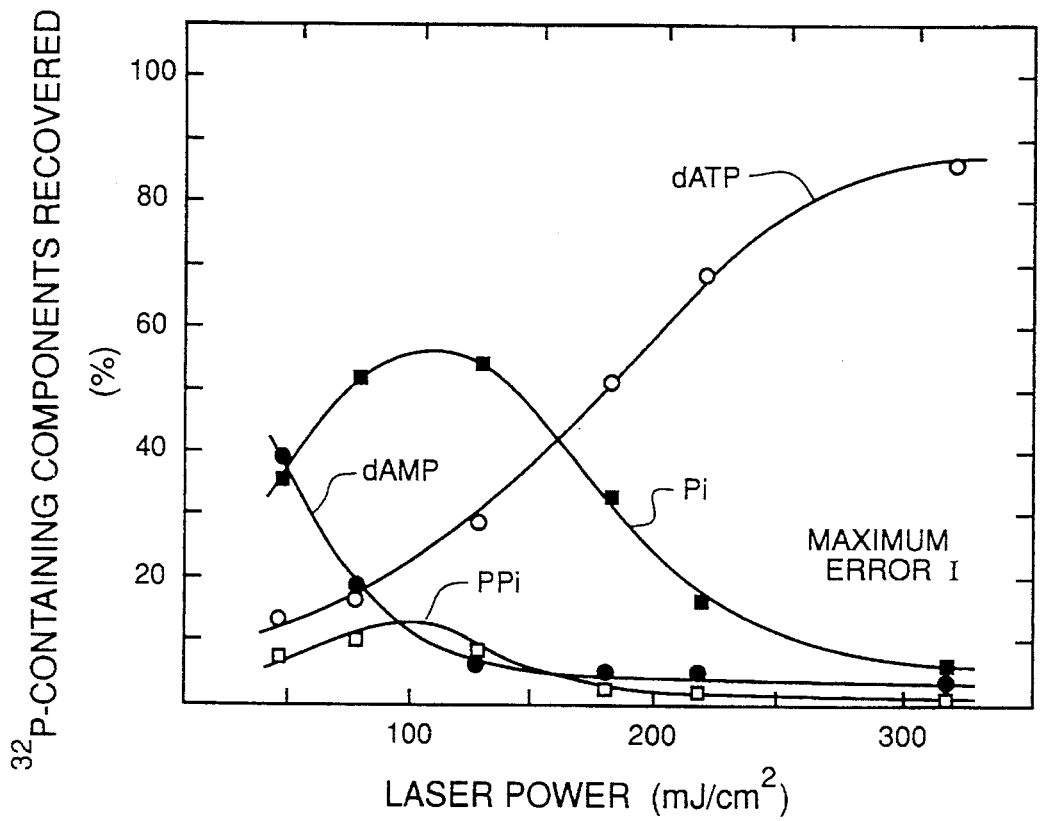
FIG. 12 is a graphical representation of the effect of laser energy on stability of dATP.

Referring to FIG. 12, each point represents the average of at least two determinations from two TLC analyses. (o) dATP, (●) dAMP, (□) pyrophosphate, and (■) phosphate. This analysis indicates that up to five species are observed in the vaporized sample, depending on the vaporization condition. As predicted from the oligonucleotide experiments described in Example 3, the highest power levels result in little decomposition of the vaporized product. At 320 mJ/cm$^2$, approximately 90% of the radioactivity present on the filter paper was recovered as dATP. What little degradation that occurred resulted in the formation of dAMP and inorganic phosphates (mono-, di- and tri-phosphates). As the laser power was reduced, several trends become evident: i) less dATP survived the laser vaporization; ii) less tripolyphosphate was observed (not shown; less than 4% was produced at even the highest power level); iii) more phosphate and diphosphate were formed; and iv) more dAMP was produced. The production of the inorganic phosphate is consistent with photochemical activation of the P-O-P bonds at intermediate vaporization power. The incident photon fluence was high enough that this activation proceeded thorough a two-photon excitation of the 274 nm electronic absorption band in the phosphate group. At the highest powers, the P-O-P bonds were still activated, but the energy was most likely quenched by collisional deactivation. At low vaporization power, the desorption mechanism became more thermal in nature. As the molecules received thermal energy, the weakest bond, the phosphodiester bond, was expected to, and observed to, break.

EXAMPLE 5

The fact that efficient molecular vaporization with very little bond breakage occurred at laser powers over 300 mJ/cm$^2$ suggested that it might be possible to effect the molecular vaporization of very long DNA strands. To test this prediction, two dideoxy DNA sequencing reactions were performed under conditions where the average chain length produced was either approximately 65 or approximately 400 nucleotides long. Two DNA sequencing reactions were carried out using SEQUENASE™ T7 DNA polymerase (United States Biochemical, Cleveland, Ohio) under conditions where the short (FIG. 13, panel A) or long (FIG. 13, panel B) DNA sequences were synthesized as described by the manufacturer.

For the reaction used to prepare short dideoxy C terminated DNA fragments (FIG. 13, panel A), a 50 µl labeling reaction was prepared containing M13mpl8 DNA, [$\alpha$-$^{32}$P] dATP and $Mn^{2+}$ buffer, using the manufacturer-recommended protocol. Immediately prior to vaporization, the DNA was denatured and mixed with rhodamine 6G. This mixture (2 µl) was spotted onto a glass cover slip. The sample was vaporized and the filters processed, as described above in Examples 2 and 3. As was found in Example 2, with the vaporization of the nucleotide and oligonucleotide, the pattern of the autoradiograms revealed virtually no evidence for spallation (not shown). The $^{32}$P-labeled materials were then eluted from the filters, and run on a high resolution polyacrylamide sequencing gel (FIG. 13). The concentrated solutions were loaded onto a denaturing 8% polyacrylamide gel and electrophoresed for 2 hr at 55 watts: FIG. 13, panel A, lane 1, 0.02 µl of the starting sequencing reaction prior to vaporization; panel A, lanes 2–5, samples recovered following vaporization at 320, 260, 210, and 160 mJ/cm$^2$, respectively.

The reaction used to prepare the long DNA sequences was virtually identical except that the Mn$^{2+}$ buffer was not used and the termination mix contained a 3:2 ratio of normal dideoxy C termination mix and extension mix. FIG. 13, Panel B, lanes 1–4, correspond to samples recovered following vaporization at 320, 260, 210, and 160 mJ/cm$^2$, respectively; panel B, lane 5 contained 0.006 µl of the starting sequencing reaction prior to vaporization. For both panels A and B, standard G, A, T, and C sequencing reactions were run in parallel in order to precisely determine the lengths of the indicated bands.

It is evident from this analysis that extremely large DNA molecules can be efficiently vaporized without any noticeable strand cleavage or degradation. In the case of the sequencing reaction containing products having an average length of 65 nucleotides (FIG. 13A), bands up to 85 nucleotides in length were visible. Longer exposures (not shown) indicated the presence of longer strands (in the 120 to 140 nucleotide range). The banding pattern for the samples generated at each of the laser powers (FIG. 13A, lanes 2–5) was as sharp as the starting material (FIG. 13A, lane 1), strongly suggesting that no strand degradation was occurring. However, unlike the 17-mer experiment, we can not rule out the possibility of trace amounts of strand scission at random position on these long strands. The intensity distributions of the vaporized samples were substantially different than that of starting sample. For example, the ratios of the 20-mer to 75-mer were compared for the two samples by densitometric scanning of the autoradiograms. The results indicated that the intensity of the 75-mer bands were reduced in relative intensity by 90% for the vaporized sample. This latter point is further strong support for molecular vaporization, since spallation would be expected to generate materials on the filters having bands intensity distributions identical to the starting samples. Similar results are obtained from the sequencing reaction carried out to give very long labeled DNA strands (FIG. 13B). Careful analysis of this gel revealed that DNA strands in excess of 1000 nucleotides long had been vaporized.

While the forms of the invention herein described constitute presently preferred embodiments, many others are possible. It is not intended herein to mention all of the possible equivalent forms or ramifications of the invention. It is understood that the terms used herein are merely descriptive rather than limiting, and that various changes may be made without departing from the spirit or scope of the invention. Other embodiments are within the following claims.

We claim:

1. A method for determining, by mass spectrometry, the nucleotide sequence of a polynucleotide comprising the steps of:

(a) generating from said polynucleotide four populations of nucleic acid molecules having from 65 to 1000 nucleotides, wherein the nucleic acid molecules of each population terminate in one of the nucleotides A, T, G or C;

(b) for each population of nucleic acid molecules forming a mixture of the nucleic acid molecules with a matrix that absorbs laser light in the visible range;

(c) vaporizing said mixture of matrix and nucleic acid molecules by illuminating with visible laser light, wherein said vaporizing occurs without fragmenting the nucleic acid molecules;

(d) ionizing the vaporized nucleic acid molecules;

(e) determining, by mass spectrometry, the molecular weight of the ionized nucleic acid molecules of each population; and (f) comparing the molecular weights of the nucleic acid molecules generated from the polynucleotide to provide the nucleotide sequence of the polynucleotide.

2. The method of claim 1, wherein said nucleic acid molecules are generated by chemical degradation of said polynucleotide.

3. The method of claim 1, wherein said nucleic acid molecules are generated by extension of a primer, complementary to a portion of said polynucleotide, by a DNA polymerase in the presence of a chain terminating agent.

4. The method of claim 3, wherein said chain terminating agent is a dideoxynucleotide triphosphate.

5. The method of claim 3, wherein said DNA polymerase is T7 DNA polymerase.

6. The method of claim 3, wherein said extension is performed in the presence of manganese.

7. The method of claim 1, wherein said polynucleotide is a DNA molecule.

8. The method of claim 1, wherein said polynucleotide is an RNA molecule.

9. The method of claim 1, wherein said comparing step is performed using a computer.

10. The method of claim 1, wherein said vaporizing step is performed using a laser adapted to emit a pulse of light.

11. The method of claim 10 wherein said vaporizing laser is adapted to emit a pulse of light having a duration of less than 10 nanoseconds.

12. The method of claim 11, wherein said vaporizing laser is adapted to emit a pulse of light of duration about 5 nanoseconds.

13. The method of claim 10, wherein the power of said laser light ranges from about 80 mJ/cm$^2$ to about 500 mJ/cm$^2$.

14. The method of claim 13, wherein the power of said vaporizing laser light is greater than about 120 mJ/cm$^2$.

15. The method of claim 13, wherein the power of said laser light is about 320 mJ/cm$^2$.

16. The method of claim 10, wherein said vaporizing laser is a neodium yttrium aluminum garnet laser.

17. The method of claim 1, wherein said illuminating is at a wavelength of from about 400 to about 1100 nm.

18. The method of claim 17, wherein said wavelength is from about 500 to about 550 nm.

19. The method of claim 18, wherein said wavelength is about 532 nm.

20. The method of claim 1, wherein said matrix is an organic dye.

21. The method of claim 20 wherein said organic dye is Rhodamine 6G.

22. The method of claim 1, wherein said matrix is selected from the group consisting of Rhodamine 6G, Rhodamine 700 or 800, DTTCI, LC8800, DNTTCI, HDITCI, DDCI-4, and dibenzocyanine 45.

23. The method of claim 1, wherein said matrix has the ability to absorb light at a wavelength of from about 400 nm to about 1100 nm.

24. The method of claim 23, wherein said matrix has the ability to absorb light at a wavelength of from about 500 nm to about 550 nm.

25. The method of claim 24, wherein said matrix has the ability to absorb light at a wavelength of 532 nm.

26. The method of claim 1, wherein said matrix absorbs light at a wavelength at which DNA does not absorb light.

27. The method of claim 1, wherein said matrix absorbs light at a wavelength at which RNA does not absorb light.

28. The method of claim 1, wherein the molar ratio of said matrix to said polynucleotide is from about 1:1 to about 100,000:1.

29. The method of claim 28, wherein said ratio is from about 1000:1 to about 25,000:1.

30. The method of claim 29, wherein said ratio is about 17,000:1.

31. The method of claim 1, wherein said nucleic acid molecule has a single positive charge.

32. The method of claim 31, wherein said single positive charge is placed on said nucleic acid molecule by resonance-enhanced multiphoton ionization.

33. The method of claim 1, wherein said nucleic acid molecule is bound to an ionizable chromophore.

34. The method of claim 33, wherein said nucleic acid molecule is chemically bound to said chromophore by a linker arm.

35. The method of claim 33, wherein said nucleic acid molecule is covalently bound to said chromophore.

36. The method of claim 33, wherein said chromophobe absorbs light having a wavelength longer than 280 nm.

37. The method of claim 34, wherein said chromophore is positioned at least 1 atom from said nucleic acid molecule.

38. The method of claim 34, wherein said chromophore is positioned less than 50 atoms from said nucleic acid molecule.

39. The method of claim 33, wherein said ionizable chromophore is a dye.

40. The method of claim 39, wherein said dye is fluorescent.

41. The method of claim 33, wherein said chromophore is selected from a group consisting of fluorescein, rhodamine, tetramethylrhodamine, sulforhodamine, nitrobenzyl-2-oxa-1-diazole, anthracene, pyrene, coumarin, acridone, N-5-dimethylaminonaphthene, and derivatives thereof.

42. The method of claim 41, wherein said derivatives are selected from the group consisting of iodoacetamide, maleimide, isothiocyanate and succinimidyl carboxylate.

43. A methods according to claim 1, wherein said ionizing is performed using a laser adapted to emitting a pulse of light.

44. The method of claim 43, wherein said laser is adapted to emit a pulse of light of less than 20 nanoseconds.

45. The method of claim 44, wherein said laser is adapted to emit a pulse of light of less than 10 nanoseconds.

46. The method of claim 1, wherein said mass spectrometer is a time-of-flight mass spectrometer.

* * * * *